(12) United States Patent
Idris

(10) Patent No.: US 6,196,220 B1
(45) Date of Patent: *Mar. 6, 2001

(54) ARTIFICIAL VENTILATION MASK

(76) Inventor: Ahamed H. Idris, 9712 SW. 1st Pl., Gainesville, FL (US) 32607

(*) Notice: Subject to any disclaimer, the term of this patent is extended or adjusted under 35 U.S.C. 154(b) by 0 days.

This patent is subject to a terminal disclaimer.

(21) Appl. No.: 09/372,440

(22) Filed: Aug. 11, 1999

Related U.S. Application Data

(63) Continuation of application No. 08/996,672, filed on Nov. 10, 1997, now abandoned, which is a continuation of application No. 08/376,177, filed on Jan. 20, 1995, now Pat. No. 5,685,298.

(51) Int. Cl.[7] .................................................. A61M 16/00
(52) U.S. Cl. ................................ 128/202.28; 128/205.12; 128/205.28
(58) Field of Search .................. 128/202.28, 202.29, 128/203.11, 204.11, 204.12, 204.13, 205.12, 205.28

(56) References Cited

U.S. PATENT DOCUMENTS

| | | | |
|---|---|---|---|
| 346,367 | * 7/1886 | Genese | 128/204.13 |
| 1,106,214 | * 8/1914 | Heilman | 128/204.11 |
| 1,695,930 | * 12/1928 | Schroder | 128/203.11 |
| 2,292,568 | * 8/1942 | Kanter et al. | 128/204.11 |
| 2,664,084 | * 12/1953 | Hammermann | 128/204.11 |
| 3,017,882 | * 1/1962 | Lewis | 128/204.11 |
| 3,099,985 | * 8/1963 | Wilson et al. | 128/203.11 |
| 3,327,704 | * 6/1967 | Bartlett, Jr. | 128/203.11 |
| 3,393,677 | * 7/1968 | Echard | 128/204.11 |
| 3,938,512 | 2/1976 | Mausteller et al. | 128/202.26 |
| 4,029,093 | 6/1977 | Kohnke | 128/203.28 |
| 4,297,117 | 10/1981 | Holter et al. | 128/205.17 |
| 4,452,241 | 6/1984 | Sarnoff et al. | 128/203.28 |
| 4,484,577 | 11/1984 | Sackner et al. | 128/203.28 |
| 4,491,130 | 1/1985 | Pasternack | 128/202.26 |
| 4,811,730 | * 3/1989 | Milano | 128/203.11 |
| 5,005,568 | * 4/1991 | Loescher et al. | 128/203.11 |
| 5,029,578 | 7/1991 | Swiatosz | 128/202.26 |

(List continued on next page.)

FOREIGN PATENT DOCUMENTS

| | | | |
|---|---|---|---|
| 646890 | 8/1962 | (CA) | 128/202.28 |
| 2517210 | 10/1976 | (DE) | 128/202.28 |

OTHER PUBLICATIONS

Michael, A.D., J.S. Forrester (1992) "Mouth–to–Mouth Ventilation: The Dying Art" Amer. J. Emer. Med. 10(2):156–160.

Ornato, J. P. et al. (1990) "Attitudes of BCLS Instructors About Mouth–to–Mouth Resuscitation During the AIDS Epidemic" Annals of Emergency Medicine 19(2):151–156.

Hermreck, A.S. (1988) "The History of Cardiopulmonary Resuscitation" The American Journal of Surgery 156:430–436.

DeBard, M.L. (1980) "The History of Cardiopulmonary Resuscitation" Ann. Emer. Med. 9(5):273–275.

Becker, L. et al. (1993) "Inhibition of Spontaneous Cardiomyocyte Contractions by Carbon Dioxide" Abstract 1203 Circulation 88(Suppl.):1–225.

(List continued on next page.)

*Primary Examiner*—Aaron J. Lewis
(74) *Attorney, Agent, or Firm*—Saliwanchik, Lloyd & Saliwanchik

(57) ABSTRACT

A mask for artificial ventilation and cardiopulmonary resuscitation is disclosed and claimed. The mask comprises a compartment which contains a material that alters the composition of the gas which is exhaled by the rescuer into the victim. The mask also provides a physical barrier between the victim and rescuer to aid in preventing the transmission of disease.

11 Claims, 2 Drawing Sheets

U.S. PATENT DOCUMENTS

| | | | |
|---|---|---|---|
| 5,095,898 | 3/1992 | Michael | 128/203.11 |
| 5,222,479 | 6/1993 | Brauer et al. | 128/202.26 |
| 5,386,825 * | 2/1995 | Bates | 128/204.13 |
| 5,394,869 | 3/1995 | Covarrubias | 128/203.29 |
| 5,685,298 * | 11/1997 | Idris | 128/202.28 |

OTHER PUBLICATIONS

Idris, A.H. et al. (1994) "Effect of ventilation on acid–base balance and oxygenation in low blood–flow states" Critical Care Medicine 22(11):1827–1833.

Idris, A.H. et al. (1994) "Effect of Ventilation on Resuscitation in an Animal Mode of Cardiac Arrest" Circulation 90(6):3063–3069.

Wenzel, V. et al. (1994) "The Composition of Gas Given by Mouth–to–Mouth Ventilation During CPR" Chest 106:1806–1810.

Idris, A.H. et al. (1992) "The Effect of Ventilation on pH1, PCO2, and End–Tidal Carbon Dioxide During Low Blood Flow States" Abstracts from the $65^{th}$ Scientific Sessions of the Circulation 1992, Circulation, Suppl. 1 86(4):1–547.

Wenzel, V. et al. (1994) "Exhaled Gas Composition of Mouth–to–Mouth Ventilation during Cardiopulmonary Resuscitation (CPR)" Crit. Care Medicine 22(1):A–133.

* cited by examiner

ARTIFICIAL VENTILATION MASK

CROSS-REFERENCE TO A RELATED APPLICATION

This is a continuation of application Ser. No. 08/996,672, filed Nov. 10, 1997 now abandoned; which is a continuation of Ser. No. 08/376,177, filed Jan. 20, 1995, now U.S. Pat. No. 5,685,298.

BACKGROUND OF THE INVENTION

Artificial respiration and cardiopulmonary resuscitation (CPR) are life-saving measures that supply necessary oxygen ($O_2$) to the blood and tissues of a patient who has experienced a cessation of normal breathing and a regular heart beat. Artificial respiration provides $O_2$ to a victim that has stopped breathing. Typically, artificial respiration can involve mouth-to-mouth ventilation (MTMV). In MTMV oxygen is provided to the victim through the expiration of the rescuer. To initiate the MTMV procedure, the rescuer opens the air-way of the victim by tilting the head of the victim back and pulling the jaw forward. The rescuer forms a seal over the mouth, or mouth and nose, of the victim with the rescuer's mouth. The rescuer then exhales into the mouth of the victim. The rescuer's exhalation is forced into the lungs of the victim and provides the victim with needed $O_2$.

Cardiopulmonary resuscitation combines mouth-to-mouth ventilation with compressions to the thorax or chest. The chest compressions push blood through the circulatory system to provide oxygen to the tissues including the heart and to remove carbon dioxide and stimulate the heart. Both procedures are used to restore normal respiratory and circulatory function or to sustain the life of a victim until adequate medical attention can be obtained.

References to procedures for artificial respiration and mouth-to-mouth ventilation have been noted for thousands of years; CPR, however, has only become an accepted practice within about the last 30 years (Hermreck, 1988; BeBard, 1980). Today, both procedures are mainstays in emergency medical situations.

Both CPR and artificial respiration can involve mouth-to-mouth contact between rescuer and victim. Therefore, concerns have arisen as to the possible transmission of communicable diseases during these life-saving procedures. Concerns have heightened recently with the emergence of AIDS. Although there have been no reported incidences of health care workers becoming HIV-positive after administering CPR to an AIDS patient, a recent survey reports that 93% of nurses surveyed would hesitate to give CPR to a patient with AIDS (Michael et al; 1992). In a survey of CPR instructors, 71% said that their attitudes about providing CPR to strangers have changed as a result of the AIDS epidemic. Forty percent of those instructors surveyed who had administered CPR in the previous three years admitted that they did hesitate before administering CPR to a victim, and over half cited a fear of disease as the cause of that hesitation (Ornato et al., 1990).

To avoid physical contact during artificial respiration and CPR, many first-aid kits now include a mask that provides a physical barrier between the mouth of the victim and the mouth of the rescuer. There are three basic types of masks routinely used for this purpose. U.S. Pat. No. 5,095,898 describes one such mask. The three main types are bag-valve masks, hand-held masks, and lay-on barrier masks. The bag-valve mask, or manual resuscitation bag, has a molded facepiece which is contoured to cover the nose and mouth of the victim. The facepiece is impermeable to air so that if properly sealed all air administered to the victim is ultimately forced into the upper airway of the victim and then into the lungs. A bag is attached to the facepiece and holds the air for ventilation. The bag-valve mask eliminates close contact between the rescuer and victim, but can prove cumbersome for a single rescuer trying to pump the bag and keep the mask sealed tightly over a victim's nose and mouth. Further, bag-valve masks usually deliver sub-optimal ventilation volumes, probably due to the lack of a proper seal.

Hand-held masks have a facepiece similar to the contoured facepiece of the bag-valve mask, but do not have a bag for ventilation. The rescuer exhales directly into an orifice in the mask. Hand-held masks therefore require more intimate contact between the rescuer and victim, but still provide a physical barrier.

Lay-on barrier masks are pliable sheets that act as a physical barrier between the mouth of the victim and the mouth of the rescuer. Lay-on barrier masks provide the greatest ventilation volume of the three types of masks. However, lay-on masks do not provide an adequate barrier to prevent contamination should a victim vomit into the mask. Further, these masks can only be used for mouth-to-mouth ventilation and cannot be connected to a bag for manual ventilation.

Because of the risks associated with mouth-to-mouth contact, debates have arisen as to the necessity of ventilating the victim during CPR. Ventilation has been found to be necessary, however, for successful resuscitation (Idris et al, 1994a; Idris et al., 1994b). Proper ventilation affects the acid-base balance as well as oxygenation of the blood of the victim, and assists in successful recovery (Idris et al., 1994b; Idris et al., 1992). Recent studies have shown that hypoxia (below normal levels of $O_2$) and hypercarbia (above normal levels of $CO_2$) in ventilating gas have independent adverse effects on resuscitation from cardiac arrest (Idris et al., 1994a; Idris et al., 1994b). The air we normally breath is approximately 21% $O_2$ and 0.033% $CO_2$. The composition of the air or gas exhaled by a rescuer is approximately 17–18% $O_2$ and 3.5–4% $CO_2$ (Wenzel et al., 1994a; Wenzel et al., 1994b). Percentages of $CO_2$ can be higher in one-rescuer CPR as opposed to two-rescuer situations. This is probably due to the greater work load that the single rescuer performing CPR must endure. Therefore, the gas composition delivered by a rescuer to a victim during CPR is both hypoxic and hypercarbic when compared to the air we normally breath. High levels of $CO_2$ have further been found to cause the inhibition of spontaneous contractions of myocardial cells in culture. This suggests that high levels of $CO_2$ may be dangerous to the heart (Becker et al., 1993).

Anesthesia machines use certain chemicals to remove carbon dioxide from gases given to a patient. Pasternak (U.S. Pat. No. 4,491,130) describes an emergency respirator which removes $CO_2$ from inhaled air when the surrounding air becomes climatically unfavorable. The respirator of Pasternak is for a user who is breathing independently. The respirator comprises a heat storage mass which captures body heat lost by the user during exhalation, and stores the heat to be supplied back to the user upon inhalation. The respirator provides the user with breathable air and prevents heat loss during respiration.

BRIEF SUMMARY OF THE INVENTION

The subject invention concerns a mask for use in artificial respiration and/or cardiopulmonary resuscitation (CPR). In a preferred embodiment, the mask of the subject invention is compact and placed over the mouth and nose of a victim in respiratory or cardiac arrest. The mask has an orifice for gas delivery through which the exhalation of the rescuer is directed into the upper respiratory tract of the victim and then into the lungs. Gas exhaled by the rescuer passes over, or through, a cartridge or compartment which contains material that alters the composition of the exhaled gas before it reaches the respiratory tract of the victim. Specifically, the material in the compartment removes carbon dioxide from the exhaled gas. In one embodiment the mask also enriches the gas with oxygen. The mask of the subject invention can further comprise an opening or valve to facilitate exit of gas exhaled by the victim.

One aspect of the subject invention pertains to a cartridge, or compartment, configured to be inserted into, or attached to, ventilation masks which lack gas altering capabilities. The compartment has contained therein a material which can advantageously alter the chemical composition of exhaled gas which comes in contact with the material. Specifically, the material can reduce the amount of carbon dioxide in the gas. The material can be, for example, calcium carbonate.

The subject invention provides an artificial ventilation mask which can be used in business locations, by emergency medical systems, on ambulances, police vehicles, and fire trucks, at mass gatherings (e.g., sporting events), and by lay public individuals. The mask improves the chemical composition of the gas which reaches the respiratory tract of the victim after being exhaled by the rescuer. In a preferred embodiment the mask removes carbon dioxide of exhaled gas and provides a physical barrier against disease.

DETAILED DESCRIPTION OF THE INVENTION

The subject invention concerns a mask for artificial ventilation and/or CPR. In a preferred embodiment, the mask comprises a compartment or cartridge containing a material that alters the composition of the gas exhaled by the rescuer and received by the victim. As use herein, reference to the "chemical compartment" includes a compartment built into a ventilation mask for the purpose of holding a material which can remove carbon dioxide and/or enrich for oxygen. Reference to "chemical compartment" further includes a cartridge which can be fitted onto or into a mask and which holds a material for removing carbon dioxide and/or enriching oxygen. The compartment and/or the material therein may be of any shape or size sufficient to effect the desired modulation of the chemical composition of the gas exhaled by the rescuer.

Figure 1:
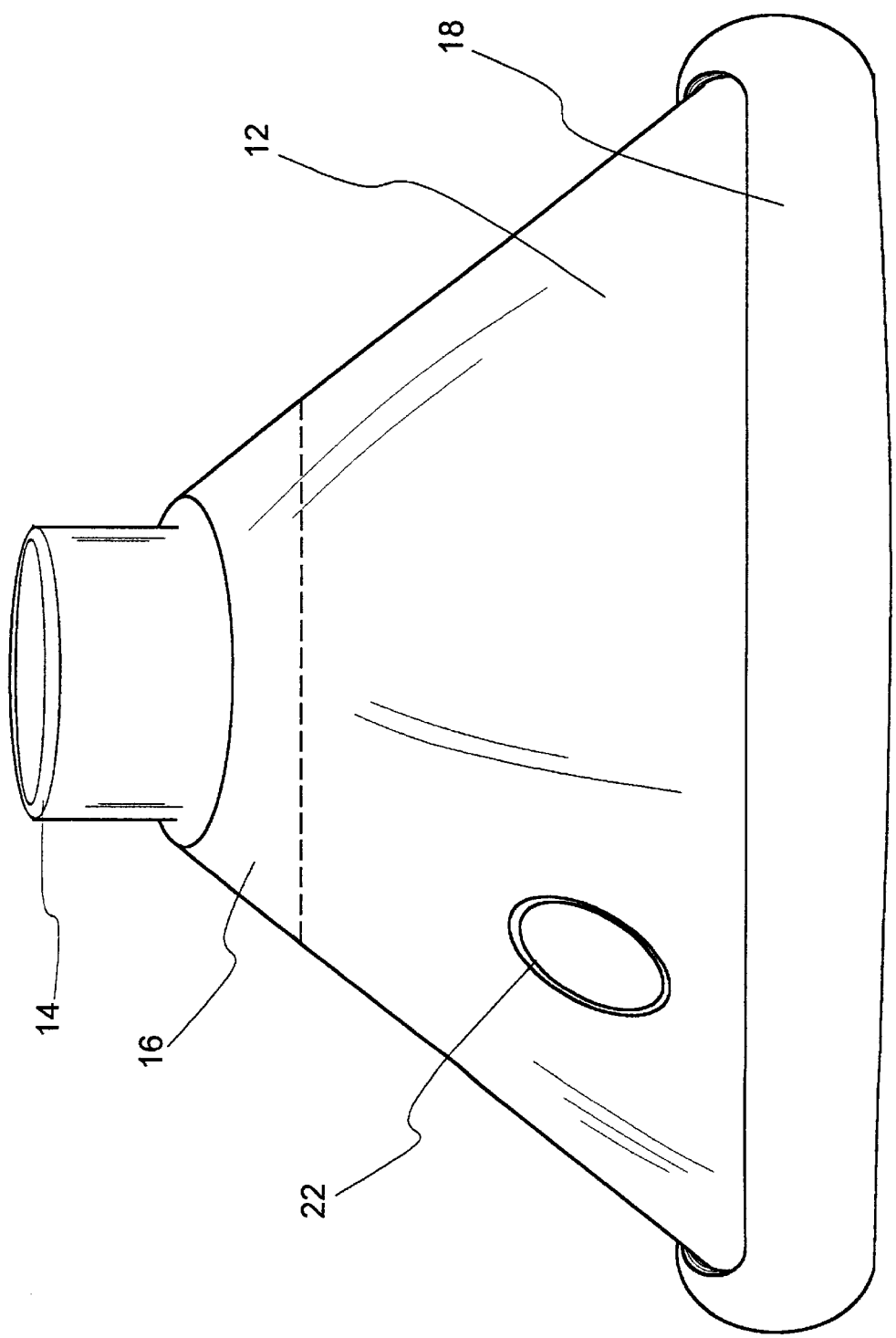
FIG. 1 shows one embodiment of the mask of the subject invention wherein the chemical compartment is an integral part of the mask.
Figure 2:
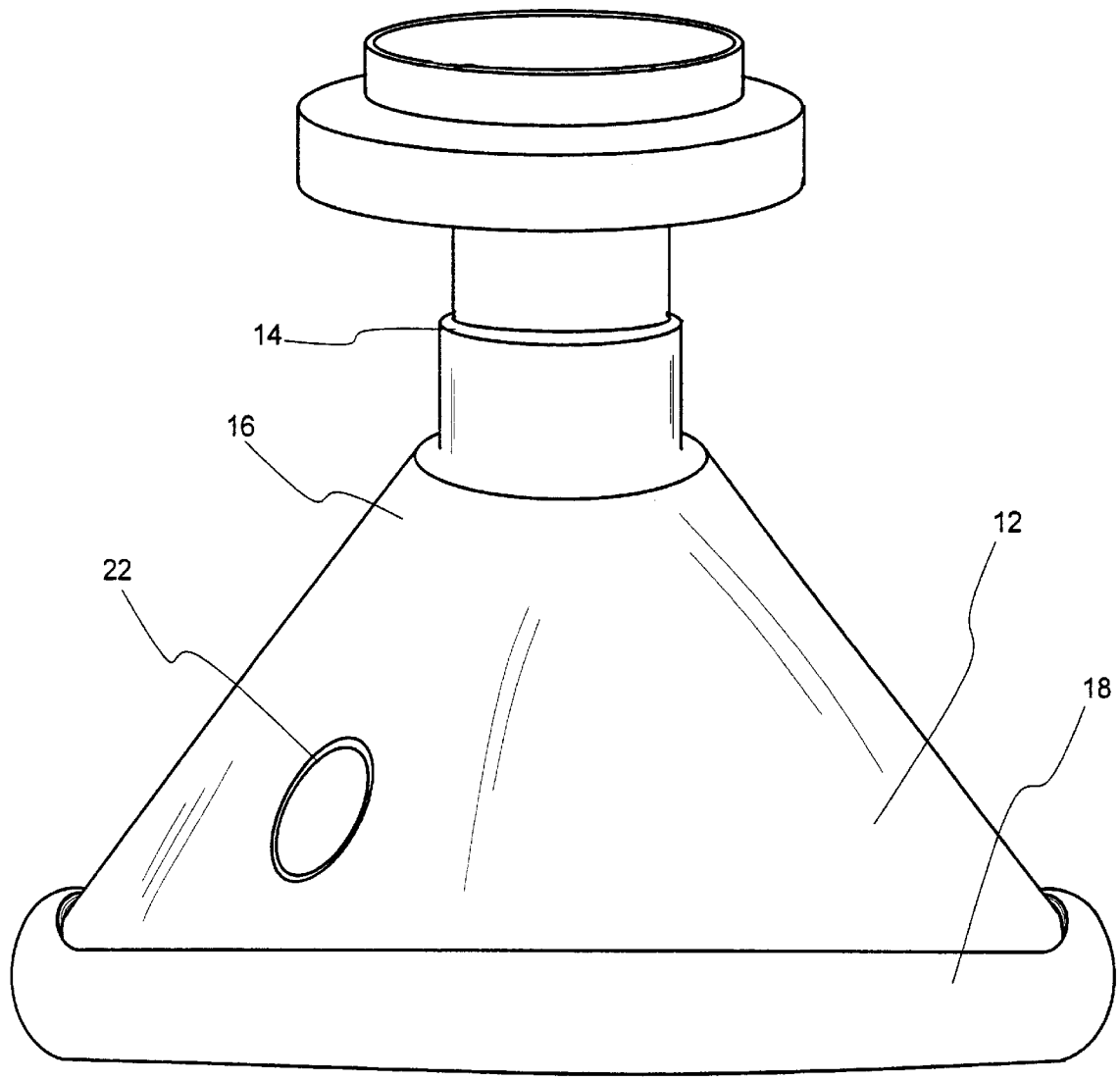
FIG. 2 shows an embodiment of the mask wherein the chemical compartment is attached to the delivery orifice of the mask.

One embodiment of the mask of the subject invention is a hand-held type mask shown in FIGS. 1 and 2. The mask comprises a barrier piece 12, a delivery orifice 14, and a chemical compartment 16. When the mask is used the barrier piece is placed over the mouth, or the nose and mouth, of the victim to exclude air from external sources and to direct the exhalation of the rescuer into the upper respiratory tract of the victim. The rescuer exhales through the delivery orifice which directs the exhaled gas over or through the chemical compartment. Contact between the exhaled gas and the material in the chemical compartment results in the removal of carbon dioxide. The material may also enrich the oxygen content. Additionally, the barrier piece provides a physical separation between the mouth of the victim and the mouth of the rescuer to avoid the transmission of communicable disease.

In a specific embodiment of the subject invention, the barrier piece 12, as shown in FIGS. 1 and 2, is a molded cup-like structure formed to fit over the nose and mouth of the victim to ensure an adequate seal between the mask and the victim and to provide the victim maximum ventilation volume. In one embodiment, the barrier piece can comprise a flexible edge portion 18 which comfortably and snugly fits against the victim's face. This flexible edge portion may be, for example, plastic, rubber, or an air-inflated bladder made from plastic, rubber, or a like material. Straps, belts, or bands can be affixed to the mask to secure the mask to the victim and assist in providing an adequate seal.

The barrier piece 12 is preferably impervious to air and most preferably also impervious to infectious agents. A barrier piece for a lay-on type mask must be pliable and be able to conform to and seal with the natural contours of the mouth of the victim. Plastic or vinyl sheets are sufficiently pliable and can be made to resist tearing. Hand-held masks, such as the mask illustrated in FIG. 1, should have a barrier piece made of a rigid or stiff material that can be molded to a smooth contour. Materials that can be used to form the cup-like barrier piece of the mask of the preferred embodiment include soft plastics and hard plastics, fiberglass, plexiglass, metal, and the like. If the barrier piece is to be reused, the material of the barrier piece should be able to withstand decontamination procedures such as treatment with harsh chemicals or autoclaving. The barrier piece can be made of a material that is either transparent or opaque. Transparent materials allow the rescuer to check the seal of the barrier piece on the victim and to determine whether the victim has vomited into the mask or the passage is otherwise blocked.

The delivery orifice 14 provides a passage through which the exhaled gas of the rescuer enters the mask. The delivery orifice can be a simple tube hermetically sealed to the barrier piece. The tube may be less than an inch long or may be a foot or more in length. The tube can be positioned on the mask so that the exhaled gas is directed across or through the chemical compartment 16 and into the mouth and nose of the victim. The direction of flow of the gas will depend upon the shape and configuration of the chemical cartridge and can be modified as necessary by one skilled in the art utilizing the teachings provided herein. The exhaled gas can be directed directly into and through a cartridge and/or may be directed across a narrower, flat cartridge, thus ensuring the exhaled gas comes into contact with maximum surface area of the chemical compartment. Further, the delivery orifice 14 can be fitted with a special mouthpiece to ensure that the delivery orifice is being held in the mouth firmly and all exhaled air is being directed into the mask. Typically, the delivery orifice may be about 15–30 mm in diameter. A mouthpiece on the delivery orifice 14 also assists a rescuer in controlling the fit and seal of the mask on the victim.

The sides of the chemical compartment should allow exhaled gas to enter the compartment, contact the material enclosed therein, and exit through the mask into the upper respiratory tract and lungs of the victim. Thus, the sides of the compartment through which exhaled gas enters and leaves the compartment must be able to contain the material within but must also allow the passage of the exhaled gas. The material from which the compartment is made may either be gas permeable or may be a fine mesh which allows the passage of gas but not the passage of the gas-altering material.

A further advantage of the subject invention is the regulation of gas flow from the rescuer to the victim. The gas flow is regulated because the rescuer must force the exhaled gas through the material in the chemical compartment.

In a preferred embodiment the chemical compartment contains materials that remove carbon dioxide. For example, chemicals such as calcium carbonate absorb $CO_2$ from the exhaled gas, reducing the partial pressure of $CO_2$. The relative partial pressure of $O_2$ can be thus increased. The chemical compartment can also comprise a material that releases oxygen as the exhaled gas passes over or through the material. For example, the material may release oxygen when exposed to moisture. The moisture may be provided by the exhaled gas itself or may be generated as the $CO_2$ in the exhaled gas is chemically removed. For example, calcium bicarbonate will release water when exposed to exhaled carbon dioxide. Carbon dioxide is removed in the process. The water produced according to this reaction can then lead to the release of oxygen upon reaction of the water with a chemical such as manganese dioxide or manganese percarbonate.

The chemical compartment can also comprise an indicator to show when the $CO_2$ absorbing properties of the material is diminished. For example, the indicator can comprise a paper strip impregnated with a pH sensitive dye or any other means which gives a rescuer a visual indication of the $CO_2$ absorption capabilities of the chemicals in the compartment at any given time. The indicator strip can also comprise printed information and thereby serve as a means of quality control or a dating system to ensure each mask will provide the recipient maximum effect.

In one embodiment, the mask of the subject invention further comprises an opening which allows the victim's exhaled gas to exit the mask without passing over or through the chemical compartment. Return of this gas through the chemical compartment provides no advantage to the victim since the victim does not rebreathe the air, and it unnecessarily spends the chemicals within the compartment. The opening 22 or an equivalent valve can be placed on the barrier piece 12 as shown in FIG. 1. The valve can be placed at the base of the delivery orifice 14 in an embodiment where the cartridge is the type that is positioned within the tube of that orifice. In either of these embodiments the hole (or holes) could be covered by the rescuer's hand or fingers as the rescuer exhales and forces gas through the mask into the upper respiratory tract and lungs of the victim.

In a further embodiment of the subject invention, the gas-altering chemicals can be contained in a cartridge which can be attached to or fitted into an existing mask. The chemical cartridge can be attached to a variety of masks in a number of ways as would be appreciated by one skilled in the art having the benefit of the teachings provided herein. The cartridge should be attached to the mask in a manner to ensure maximum contact of the rescuer's exhalation with the gas-altering chemicals. A cartridge can be formed to fit snugly against the orifice of hand-held masks and can be held in place by friction or tension. Masks can be specially constructed to comprise brackets or pockets to hold the chemical cartridge. The cartridge can be shaped to fit into and be retained by the tube of the delivery orifice. Lay-on masks can comprise pockets into which a bean-bag like chemical cartridge can be slipped, wherein the free-form of the cartridge conforms to the victim's mouth to ensure that all gas entering the victim has passed through the cartridge.

In an additional embodiment of the subject invention, the chemical compartment can comprise medications which can be volatilized and delivered through the pulmonary route during rescue. Such medications would include, but not be limited to, medications to treat asthma or heart failure, or other conditions which can cause cessation or extreme difficulty in breathing. Such medications could include, for example, epinephrine. In this embodiment of the subject invention the mask would preferably comprise a valve which would prevent any backflow of gas.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Michael, A. D., and J. S. Forrester (1992) "Mouth-to-Mouth Ventilation: The Dying Art," *Amer. J Emer. Med.* 10(2):156–161.

Ornato, J. P., L. F. Hallagan, S. B. McMahon, E. H. Peeples, and A. G. Rostafinski (1990) "Attitudes of BCLS Instructors About Mouth-to-Mouth Resuscitation during the AIDS Epidemic," *Ann. Emer. Med.* 19(2):151–156.

Hermreck, A. S. (1988) "The History of Cardiopulmonary Resuscitation," *Amer. J. Surgery* 156:430–436.

DeBard, M. L. (1980) "The History of Cardiopulmonary Resuscitation, " *Ann. Emer. Med.* 9(5):273–275.

Becker, L., A. Idris, Z. Shao, C. Lir, J. Art, S. Schorer, M. Goodman and R. Zak (1993) "Inhibition of Spontaneous Cardiomyocyte Contractions by Carbon Dioxide," Abstract 1203 *Circulation* 88(Suppl.):I-225.

Idris, A. H., E.D. Staples, D. J. O'Brien, R. J. Melker, M. J. Rush, K. D. DelDuca and J. L. Falk (1994a) "The Effect of Ventilation on Acid-Base Balance and Oxygenation in Low Blood Flow States," *Crit. Care Med.* 22:1827–1834.

Idris, A. H., L. B. Becker, R. S. Fuerst, V. Wenzel, W. J. Rusch and R. J. Melker (1994b) "The Effect of Ventilation on Resuscitation in an Animal Model of Cardiac Arrest," *Circulation* 90:3063–3069.

Wenzel, V., A. H. Idris, M. J. Banner, R. S. Fuerst, and K. J. Tucker (1994a) "The Composition of Gas Given by Mouth-to-Mouth Ventilation During CPR," *Chest* 106:1806–1810.

Idris, A. H., R. J. Melker, K. D., DelDuca, E. D. Staples, D. J. O'Brien, W. Rush, J. L. Falk (1992) "The Effect of Ventilation of pH, $PCO_2$ and End-Tidal Carbon Dioxide During Low Blood Flow States," Abstracts from the 65th Scientific Sessions of the Circulation 1992, *Circulation, Suppl. I* 86(4):I-547

Idris, A. H., R. S. Fuerst, V. Wenzel, L. B. Becker, D. J. Orban and M. J. Banner (1993b) "Does Hypoxia or Hypercarbic Acidosis Independently Affect Survival from Cardiac Arrest?." *Circulation* 88(Suppl.):I-225.

Wenzel, V., A. H. Idris, M. J. Banner, R. S. Fuerst, and D. J. Orban (1994b) "Exhaled Gas Composition of Mouth-to-Mouth Ventilation During Cardiopulmonary Resuscitation (CPR)," *Crit. Car. Med.* 22:A-133.

What is claimed is:

1. A mask for artificial ventilation or cardiopulmonary resuscitation to deliver an exhaled gas having a chemical composition from a rescuer to a victim, wherein said mask comprises:

(a) a barrier piece to cover a victim's mouth or such a victim's nose and mouth, (b) a gas delivery orifice, and;

(c) a compartment comprising a material which is able to alter said chemical composition of the delivered gas, wherein said gas delivery orifice is positioned such that gas exhaled by such a rescuer into said gas delivery orifice contacts said gas-altering material before entering a victim's upper respiratory tract and lungs.

2. The mask, according to claim 1, wherein the material within said compartment alters the composition of said delivered gas by decreasing the partial pressure of carbon dioxide in said gas.

3. The mask, according to claim 1, wherein the material within said compartment alters the composition of said delivered gas by increasing the partial pressure of oxygen in said gas.

4. The mask, according to claim 1, wherein the material in said compartment comprises a carbonate.

5. The mask, according to claim 4, wherein the material in said compartment comprises calcium carbonate.

6. The mask, according to claim 1, wherein said barrier piece is molded to conform to the nose and mouth of such a victim.

7. The mask, according to claim 1, wherein a material within said compartment releases oxygen when contacted by such a rescuer's exhaled gas.

8. The mask, according to claim 7, wherein the material within said compartment which releases oxygen is selected from the group consisting of manganese dioxide and manganese percarbonate.

9. The mask, according to claim 1, wherein the material which alters the gas composition comprises calcium carbonate.

10. The mask, according to claim 1, which comprises a hole or valve to allow gas exhaled by the victim to leave the mask without contacting the gas-altering material.

11. The mask, according to claim 1, wherein said material which alters the gas composition comprise a medicament.

* * * * *